United States Patent [19]

Shim

[11] 4,348,291
[45] Sep. 7, 1982

[54] NOVEL PHOSPHORAMIDES, LUBRICATING COMPOSITIONS AND METHOD OF IMPROVING WEAR AND EXTREME PRESSURE CHARACTERISTICS OF LUBRICATING OIL

[75] Inventor: Kyung S. Shim, Irvington, N.Y.

[73] Assignee: Stauffer Chemical Company, Westport, Conn.

[21] Appl. No.: 54,126

[22] Filed: Jul. 2, 1979

[51] Int. Cl.$^3$ .............................................. C10M 1/44
[52] U.S. Cl. .................................. 252/49.9; 252/46.6; 260/937
[58] Field of Search ........................... 252/46.6, 49.9; 260/737

[56] References Cited

U.S. PATENT DOCUMENTS

| | | | |
|---|---|---|---|
| 2,661,365 | 12/1953 | Gamrath et al. | 252/46.6 X |
| 2,712,029 | 6/1955 | Van Winkle et al. | 252/49.9 X |
| 3,270,093 | 8/1966 | Gradsten | 260/937 |
| 3,321,401 | 5/1967 | Ford et al. | 252/49.9 X |
| 3,767,733 | 10/1973 | Dulog et al. | 252/49.9 X |
| 3,795,612 | 3/1974 | Stournas et al. | 252/46.6 |
| 3,795,613 | 3/1974 | Hotten | 252/49.9 |
| 3,803,038 | 4/1974 | Olszewski | 252/49.9 |
| 3,846,317 | 11/1974 | Lintzenich | 252/49.9 X |
| 3,867,297 | 2/1975 | Nebzydoski et al. | 252/47.5 |
| 3,879,497 | 4/1975 | Nudenberg et al. | 260/937 X |
| 3,905,908 | 9/1975 | Haugen | 252/49.9 |
| 4,007,236 | 2/1977 | Duffy et al. | 260/937 X |

Primary Examiner—Andrew Metz
Attorney, Agent, or Firm—Roger S. Benjamin

[57] ABSTRACT

Novel phosphoramides of the formula:

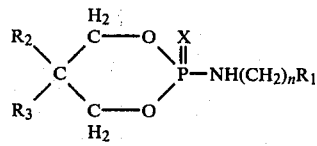

wherein:
 n is 3 to 8;
 $R_1$ is a mono- or di-alkylamine or alkenyl having a total of from 8 to 20 carbon atoms;
 $R_2$ and $R_3$ are each, independently, alkyl of 1 to 3 carbon atoms; and
 X is oxygen or sulfur.

The compounds, when combined with a lubricating oil (such as a mineral oil fraction or synthetic ester oil) or grease of appropriate lubricating viscosity are effective in improving the wear or extreme pressure lubricating characteristics of such oils or greases. Lubricating compositions containing such phosphoramides and methods for improving the wear or extreme pressure lubricating characteristics of oils or greases using such phosphoramides are also provided.

7 Claims, No Drawings

NOVEL PHOSPHORAMIDES, LUBRICATING COMPOSITIONS AND METHOD OF IMPROVING WEAR AND EXTREME PRESSURE CHARACTERISTICS OF LUBRICATING OIL

BACKGROUND

1. Field of the Invention

This invention relates to certain new phosphoramides and to improved lubricating compositions containing the same. A particular aspect of this invention relates to the improvement in the wear or extreme pressure characteristics of oils or greases by the addition thereto of certain phosphoramides.

2. Prior Art

It is known that sliding or rubbing metal or other solid surfaces are subject to wear under conditions of extreme pressure. Wearing is particularly acute in modern engines in which high temperatures and high contact pressures are prevalent. Under such conditions, severe erosion of metal surfaces can take place, even with lubricants of ever increasing sophistication, unless a load carrying additive is present. As a consequence, much effort has been expended to discover additives useful in preventing such wear. For example, U.S. Pat. No. 3,846,317 to Lintzenich describes phosphoramidates of triazoles, such as 1, 2, 4 triazole, effective as load carrying agents, corrosion inhibitors, anti-oxidants, and to increase the stability of lubricant compositions. The entire disclosure of Lintzenich is incorporated herein by reference.

SUMMARY OF THE INVENTION

Generally, the novel phosphoramides contemplated by this invention improve the wear or extreme pressure lubricating characteristics of a lubricating oil or grease.

It is an object of this invention to provide new compounds, which when combined with an oil or grease of appropriate lubricating viscosity, are effective to improve the wear or extreme pressure lubricating characteristics of such oils or greases.

It is another object of this invention to provide a lubricating oil or grease having improved wear or extreme pressure lubricating characteristics.

It is still another object of this invention to provide a method for improving the wear or extreme pressure lubricating characteristics of an oil or grease.

The novel phosphoramides of this invention have the formula:

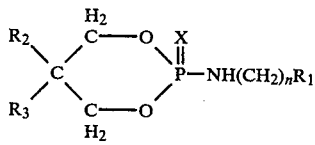

wherein:

n is 3 to 8;

$R_1$ is a mono- or di-alkylamine or alkenyl having a total of from 8 to 20 carbon atoms;

$R_2$ and $R_3$ are each, independently, alkyl of 1 to 3 carbon atoms; and

X is oxygen or sulfur.

Another aspect of this invention is to provide a lubricating composition which comprise a major amount of a lubricating oil or grease of suitable lubricating viscosity, and a wear or extreme pressure improving amount of the aforementioned novel phosphoramides.

Another aspect of this invention is a method of improving the wear or extreme pressure lubricating characteristics of a lubricating oil or grease comprising adding to the oil a wear or extreme pressure improving amount of the aforementioned novel phosphoramides.

DETAILED DESCRIPTION OF THE INVENTION

Preferably $R_1$ is an alkenyl substituent having 10 carbon atoms or an —$NHR_4$ substituent, wherein $R_4$ is alkyl having 18 carbon atoms. It is further preferred that $R_2$ and $R_3$ both be —$C_3$ substituents and n be 3 or 8. The oxygen analogs are highly preferred, i.e. X is oxygen.

Two particularly preferred phosphoramides of this invention having the following formula:

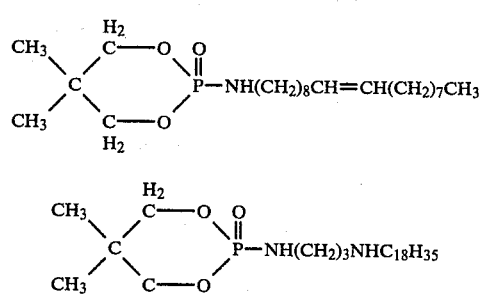

Compounds having sulfur substituted for oxygen in the

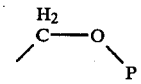

grouping are equivalent in this invention to the aforementioned novel compounds.

In general, the compounds of this invention are made by employing reactions well known in the art, see for example, U.S. Pat. No. 3,846,317 to Lintzenich. Broadly, the compounds are formed by the following reaction:

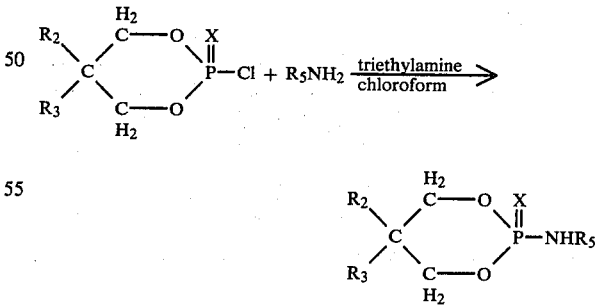

wherein $R_2$ and $R_3$ are as previously defined; and $R_5$ is —$(CH_2)_nR_1$ wherein $R_1$ and n are as previously defined.

The novel compounds of this invention can be used in a wide variety of lubricant media. Thus, they are effective agents for lubricating oils such as mineral oils, both naphthenic and paraffinic, including those containing substantial amounts of aromatic oils. They are also effective for synthetic oils, such as synthetic hydrocarbons which are obtained by polymerizing olefins, synthetic esters and polysiloxanes and the like. The term "lubricant" also includes greases made from any of the mentioned lubricating oils by adding a grease forming agent thereto. Particularly preferred synthetic ester oils of importance are those made by reacting carboxylic acids with certain polyols.

When used for the purposes herein disclosed, the additives are effective at from about 0.02% by weight to about 10% by weight, preferably from about 1.0% to about 2.0%.

The following examples will serve to illustrate the invention. It should be kept in mind that they are for illustration only and are not intended to limit the inventive scope.

EXAMPLE 1

Preparation of phosphoramide

The phosphoramide of the following formula:

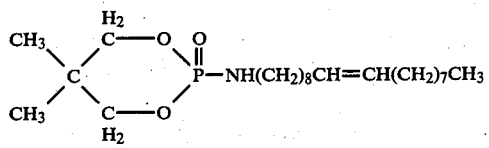

was prepared by reacting in equimolar quantities, methyl substituted 1,3-dioxa-2-oxo-2-chlorophosphorinane of the formula:

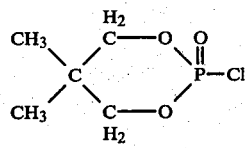

(36.9 grams 0.2 moles) with oleylamine (53.5 grams, 0.2 moles) in the presence of triethylamine (22 grams, 0.22 moles) and chloroform (200 ml.).

The chlorophosphorinane and chloroform were placed in a 500 ml. flask. A mixture of oleylamine and triethylamine was added dropwise, with stirring. The reaction became exothermic. Upon cooling to room temperature a white solid precipitate began to appear. The mixture was washed with water, dried over magnesium sulfate, filtered and stripped in a rotary evaporator. 67 grams of product were produced. An elemental analysis was performed indicating 6.82% phosphorus (7.5% theoretical) and 3.71% nitrogen (3.4% theoretical).

EXAMPLE 2

Preparation of Phosphoramide

The phosphoramide of the following formula:

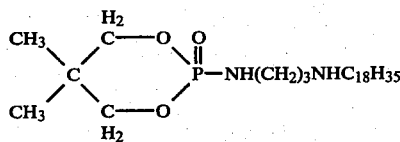

was produced using the same chlorophosphorinane as used in Example 1 and reacting it with N-oleyl-1,3-diamine propane (65.1 grams, 0.2 moles). The same quantities of chlorophosphorinane (36.9 grams, 0.2 moles), triethylamine and chloroform were used, as well as the same procedure. Ninety-six (96) grams of product were produced having an elemental analysis of 5.7% phosphorus (6.5% theoretical) and 5.1% nitrogen (5.9% theoretical).

EXAMPLE 3

Four Ball Method Tests

The wear preventitative characteristics of a lubricating composition containing the compound of Example 1 were tested by the Four Ball Method, ASTM Designation: D 2266-67 (Reapproved 1972), a widely accepted repeatable screening test for testing lubricants for extreme pressure lubricating characteristics. The Four Ball Method was utilized at 40 kg, 1 hour, 54° C. at 1800 rpm. The concentration of the compound of Example 1 was 1.0% in a paraffinic mineral oil of 150 SUS. The scar diameter was 0.51 mm. The test was repeated at 0.5 wt.% concentration resulting in a scar diameter of 0.20 mm.

The same test was repeated at 0.5 wt.% concentration using ASTM-3 reference oil, i.e. a naphthenic oil, resulting in a scar diameter of 0.40 mm.

The scar diameter for the paraffinic mineral oil without any additive was 1.89 mm. The scar diameter for the ASTM-3 reference oil without any additive was 1.92 mm.

The compound of Example 1 was further tested at a concentration of 0.5% in a di-tridecyl adipate diester (TDA) synthetic lubricating oil resulting in a scar diameter of 0.38 mm. The TDA lubricant without any additive had a scar diameter of 1.72 mm.

EXAMPLE 4

Four Ball Method

The Four Ball Method was used to test the compound of Example 2 under the same conditions indicated in Example 3. Using the paraffinic mineral oil, with 0.1% concentration of the compound of this invention resulted in a scar diameter of 0.43 mm.; at a concentration of 1.0% the scar diameter was 0.37 mm.

Using ASTM-3 reference oil with 0.1% concentration of the compound of this invention (Example 2) resulted in a scar diameter of 0.43 mm.; and at a concentration of 1.0% a scar diameter of 0.48 mm.

What is claimed is:

1. The compound of the formula:

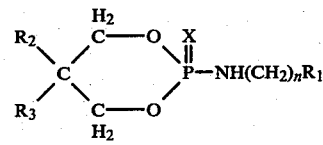

wherein:
n is 3 to 8;
$R_1$ is a mono- or di-alkylamine or alkenyl, having a total of from 8 to 20 carbon atoms;
$R_2$ and $R_3$ are each, independently, alkyl of 1 to 3 carbon atoms; and
X is oxygen or sulfur.

2. The compound of claim 1, wherein $R_1$ is alkenyl having 10 carbon atoms or —$NHR_4$ wherein $R_4$ is alkyl having 18 carbon atoms; $R_2$ and $R_3$ are —$CH_3$; and X is oxygen.

3. The compound of claim 2, wherein n is 3 or 8.

4. The compound having the formula:

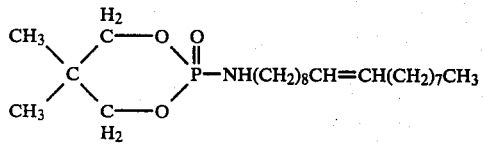

5. The compound having the formula:

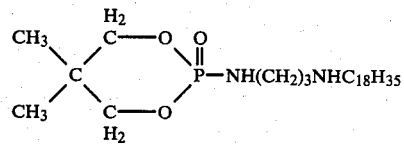

6. A lubricating composition comprising a major amount of lubricating oil or grease and a wear or extreme pressure improving amount of the compounds of claims 1, 2, 3, 4 or 5.

7. A method of improving the wear or extreme pressure lubricating characteristics of a lubricating oil or grease comprising adding to the lubricating oil or grease a wear or extreme pressure improving amount of the compounds of claims 1, 2, 3, 4 or 5.

* * * * *

UNITED STATES PATENT AND TRADEMARK OFFICE
CERTIFICATE OF CORRECTION

PATENT NO. : 4,348,291
DATED : September 7, 1982
INVENTOR(S) : Kyung S. Shim

It is certified that error appears in the above-identified patent and that said Letters Patent are hereby corrected as shown below:

Column 2, line 14, "be-$C_3$" should be -- be-$CH_3$ --.

Signed and Sealed this

Fourteenth Day of February 1984

[SEAL]

Attest:

GERALD J. MOSSINGHOFF

Attesting Officer

Commissioner of Patents and Trademarks